| [19] | | [11] | 4,141,917 |
|---|---|---|---|
| United States Patent | | | |
| Kunstmann et al. | | [45] | Feb. 27, 1979 |

[54] PROCESS FOR THE PREPARATION OF TRIAMINO BENZENES BY CATALYTIC HYDROGENATION OF 2,4-DINITRO ANILINES

[75] Inventors: Walter Kunstmann, Neuenhain, Taunus; Bernhard Mees, Königstein, Taunus, both of Fed. Rep. of Germany

[73] Assignee: Hoechst Aktiengesellschaft, Frankfurt am Main, Fed. Rep. of Germany

[21] Appl. No.: 629,678

[22] Filed: Nov. 6, 1975

[30] Foreign Application Priority Data

Nov. 8, 1974 [DE]  Fed. Rep. of Germany ....... 2453055

[51] Int. Cl.$^2$ ............................................. C07C 85/11
[52] U.S. Cl. .................................. 260/580; 260/578; 548/305
[58] Field of Search ........................................ 260/580

[56] References Cited

U.S. PATENT DOCUMENTS

| 2,684,383 | 7/1954 | Krueger .................. 260/575 |
| 3,079,435 | 2/1963 | Friefelder et al. .................. 260/562 |
| 3,366,683 | 1/1968 | Johnson et al. .................. 260/570.9 |
| 3,929,891 | 12/1975 | Habig et al. .......................... 260/580 |
| 3,935,264 | 1/1976 | Bhutani ............................... 260/580 |

OTHER PUBLICATIONS

Adams et al., "JACS", vol. LXXIX, pp. 417–419 (1957).
Webster, "Webster's Third International Dictionary", p. 961 (1961).
Sidgwick, "Organic Chem. of Nitrogen", pp. 252, 256 & 257 (1949).
Astle, "Industrial Organic Nitrogen Compounds", pp. 84–87 (1961).
Tickle et al., "J. Chem. Soc. B", vol. 1, pp. 65–70 (1970).

*Primary Examiner*—Winston A. Douglas
*Assistant Examiner*—John Doll
*Attorney, Agent, or Firm*—Curtis, Morris & Safford

[57] ABSTRACT

1,2,4-triamino benzenes are obtained in high yield and purity by catalytic hydrogenation of 2,4-dinitro anilines in water containing at least one molar equivalent of a mono- or di-carboxylic acid. The products are known and useful as intermediates for dyes and biocides.

12 Claims, No Drawings

PROCESS FOR THE PREPARATION OF TRIAMINO BENZENES BY CATALYTIC HYDROGENATION OF 2,4-DINITRO ANILINES

The present invention relates to a process for the preparation of 1,2,4-triamino-benzenes.

It is already known that dinitro-anilines can be reduced in hydrochloric acid with tin according to the Hinsberg method. That method, however, has its drawbacks due to pool yields (41%) and to a heavy waste water pollution by metal salts, which can no longer be accepted by current standards. It is also known catalytically to reduce dinitro-anilines in organic solvents, such as methanol, ethanol or toluene, using hydrogen. That method, however, entails work-up difficulties, since admissible Threshold Limit Values must be observed, and the organic solvent has to be regenerated, thus raising the costs of the process. Moreover, there are great risks involved in using alcohols as readily oxidizable substances in conjunction with the polynitro compounds which have a strong oxidizing effect.

Attempts catalytically to hydrogenate dinitro-anilines in water using industrial-scale catalyst concentrations of from 1 to 12% by weight, calculated on dinitro-analine used, result in a product that contains a number of contaminants, for example in the reduction of 6-chloro-2,4-dinitro-aniline to the corresponding triamine. The resulting solution displays a distinct ammonia odor, i.e. the hydrogenation must have split off amino groups. The addition of alkaline substances to the aqueous suspension of the dinitro-aniline prior to hydrogenation, as disclosed in the art for the catalytic reduction of nitro-anilines to diamines, does not produce a positive effect.

It has now been found that 1,2,4-triamino-benzenes of the formula

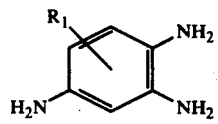

in which $R_1$, if linked in 6-position, stands for a hydrogen atom, a halogen atom, preferably a chlorine atom, or the methyl group, and if linked in 5-position, stands for a hydrogen atom or the methyl group, are obtained in good yield and purity by adding, in the catalytic reduction of 2,4-dinitro-aniline of the formula

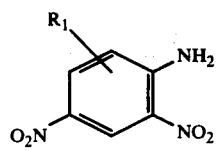

in which $R_1$ is defined as above, an organic mono- or dicarboxylic acid of the general formula

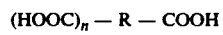

$(HOOC)_n - R - COOH$ in which n stands for zero or 1, and , if n is zero, R stands for a hydrogen atom, a phenyl group or an alkyl group of 1 to 4 carbon atoms, and if n is 1, R means a direct bond, a phenylene group or an alkylene group of 1 to 4 carbon atoms.

The process of the invention is carried out by suspending dinitro-anilines in water in a hydrogenation autoclave, adding said organic acid, then a hydrogenation catalyst, pressurizing with hydrogen and effecting hydrogenation. The reaction conditions concerning temperature, concentration, molar ratio of dinitro-aniline and acid may be varied greatly; the temperature chosen generally ranging from about 50 to 130° C., preferably from about 70 to 100° C.

An upper limit to the concentration of dinitro-aniline in water is merely set by the requirement that the resulting suspension can be stirred. Ample dilution has no adverse effect on this process. To achieve an optimum space-time yield and an ease of the reaction mixture being stirred, about 700 to 800 parts by volume of water are preferably used per mol of dinitro-aniline. The acid concentration's upper limit only depends on an economical handling of the process, while its lower limit is subject to a steady decrease in efficiency if per one mol of dinitro-aniline less than one equivalent of acid is added, i.e. when a dicarboxylic acid is used, a ratio of 0.5 mol of acid to 1 mol of dinitro-aniline is adquate. The carboxylic acids used are preferably weak aliphatic monocarboxylic acids, such as acetic acid, optionally with an addition of their alkali metal salts for buffering purposes. However, dicarboxylic acids may also be used successfully as they can be regenerated by simple filtration at room temperature owing to their low solubility in water, for example adipic acid or terephthalic acid.

As hydrogenation catalysts, the known noble metal catalysts may be used, but preferably the less expensive commercial-type nickel catalysts in an amount usual for catalytic reductions.

The yield and purity of the triamine obtained by the catalytic reduction cannot be characterized by the usual criteria, such as weight and melting point. These aromatic triamines are so sensitive to autoxidation that, as free bases, they cannot be isolated in a pure form.

Characterization of the triamines is therefore made via the urea derivative of the formula

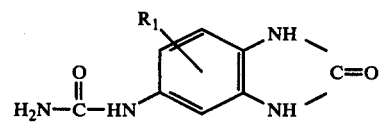

Such a urea derivative is obtained by adding 5 mols of urea per mol of triamine after reduction and refluxing the mixture for about 5 hours while maintaining the pH-value between 4 and 5 by means of an acid. The precipitated urea compound is then suction-filtered and dried. The yield obtained serves as a basis for calculating the yield of triamine after the catalytic reduction.

The process of the present invention permits catalytic hydrogenation of dinitro-anilines in an aqueous suspension. With regard to a reduction in hydrochloric acid using tin, this process is distinguished by higher yields and a substantially reduced waste water pollution. Compared with the catalytic hydrogenation of dinitro-anilines in organic solvents, the instant process is far more economical since no such solvent is required nor need to be regenerated. Another advantage of this process is that inexpensive nickel catalysts currently employed in industry can be used as hydrogenation catalysts instead of noble metal catalysts, such as platinum or palladium compounds.

A vital advantage is that the triamines obtained in an aqueous solution after reduction can be processed directly, i.e. without intermediate isolation. For example, an aqueous solution of 1,2,4-triamino-benzene can be converted in the usual manner, after acidification, into the diazonium salt of 5-amino-benzo-triazole by a reaction with a corresponding amount of a sodium nitrite solution.

The aromatic triamines are valuable intermediate products for dyes and pesticides.

The following Examples illustrate the invention, the parts and percentages being by weight unless stated otherwise, and the ratio of parts by weight to parts by volume being that of kilogram to liter.

EXAMPLE 1

109 Parts of finely ground 6-chloro-2,4-dinitro-aniline together with 73 parts of adipic acid, 10 parts of a commercial-type nickel catalyst (about 50% Ni on kieselguhr) and 500 parts by volume of water charged into a hydrogenation autoclave equipped with a double-acting, magnetically operated agitator. After the autoclave had been sealed, air was expelled from the free volume by passing nitrogen over it (for 15 minutes). Heating and agitator were then put to work, 120 atmsg. of hydrogen were forced in under pressure, and hydrogenation was effected. Hydrogen absorption started at about 60° C., and was complete within about 2 hours at a maximum temperature of 95° C. Evidence for 6-chloro-1,2,4-triamino-benzene obtained was provided by releasing the residual hydrogen, freeing the mixture from the catalyst by filtration through a pressure filter under a nitrogen pressure of 20 atmsg. and passing the filtrate into another stirrer-equipped vessel which contained 150 parts of urea. The mixture was then refluxed for 5 hours while maintaining the pH at 4 - 5 by adding a total of about 112 parts of sulfuric acid monohydrate. The ph was then adjusted to 6 by means of 54 parts of a 33% sodium hydroxide solution, and the mixture was cooled to room temperature. About 90 parts of a compound were obtained, which has a melting point of 341° C. and whose analytical data for C, H, Cl and N corresponded to the calculated values for the urea compound of the formula

|  | C | H | N | Cl |
|---|---|---|---|---|
| Analysis: | | | | |
| found: | 42.8 | 3.20 | 24.82 | 15.4 |
| calculated: | 42.5 | 3.12 | 24.79 | 15.69 |
| $C_8H_7N_4ClO_2$ molecular weight: 226.5 | | | | |

EXAMPLE 2

109 Parts of finely ground 6-chloro-2,4-dinitro-aniline together with 60 parts of glacial acetic acid and 20 parts of a 33% sodium hydroxide solution, 10 parts of a commercial-type nickel catalyst and 500 parts by volume of water were charged into a hydrogenation autoclave equipped with a double-acting, magnetically operated agitator. After the autoclave had been sealed, hydrogenation was effected in the usual manner (as in Example 1). After the reaction with urea in the presence of sulfuric acid at pH 4–5, 87 parts of the urea compound described in Example 1 were obtained, corresponding to a theoretical yield of 77%, calculated on 6-chloro-2,4-dinitro-aniline used.

EXAMPLE 3

91 Parts of finely ground 2,4-dinitro-aniline together with 73 parts of adipic acid, 10 parts of a commercial-type nickel catalyst and 400 parts by volume of water were charged into a hydrogenation autoclave. After the autoclave had been sealed, hydrogenation was effected in the usual manner at a temperature ranging from 60 to 100° C., while keeping the hydrogen pressure constant for about half an hour after the end of hydrogenation. For evidencing 1,2,4-triamino-benzene obtained, residual hydrogen was released, and the mixture was freed from the catalyst by filtration through a pressure filter under 20 atmsg. nitrogen and the filtrate passed into another flask flushed with nitrogen. The urea compound was prepared as described in Example 1. 62 Grams of a compound having a melting point higher than 335° C. were obtained. The following table shows accordance of the analytical data with the calculated values of the formula

|  | C | H | N |
|---|---|---|---|
| Found: | 51.0 | 4.25 | 29.5 |
| Calculated: | 50.04 | 4.2 | 29.18 |
| $C_8H_8N_4O_2$ molecular weight: 191 | | | |

After the filtration of the urea compound, the adipic acid was recovered by acidifying the filtrate to pH 2 and utilized again without further purification.

EXAMPLE 4

98 Parts of finely ground 5-methyl-2,4-dinitro-aniline togehter with 83 parts of terephthalic acid, 10 parts of a commercial-type nickel catalyst and 600 parts by volume of water were charged into a hydrogenation autoclave and hydrogenated in the usual manner. After hydrogenation as complete, the existance of the resulting 5-methyl-1,2-4-triamino-benzene was demonstrated by separating the catalyst by filtration and reacting the filtrate under a nitrogen atmosphere as described to yield the urea compound. 72 Grams of a compound were obtained, which had a melting point of 280° C. and whose analytical data for C, H, N corresponded to the values calculated for the urea compound:

|  | C | H | N |
|---|---|---|---|
| Found: | 51.8 | 4.87 | 27.5 |
| Calculated: | 52.47 | 4.9 | 27.2 |
| $C_9H_{10}N_4O_2$ molecular weight: 206 | | | |

EXAMPLE 5

98 Parts of finely ground 6-methyl-2,4-dinitro-aniline together with 61 parts of benzoic acid, 15 parts of a commercial-type nickel catalyst and 550 parts by volume of water were filled into a hydrogenation autoclave. Hydrogenation was performed in the usual manner at a temperature of from 100 to 120° C., and the catalyst was then separated. After reaction of the triamino compound (6-methyl-1,2,4-triamino-benzene) with urea, 72 g of a compound were obtained which had a melting point of 320° C, and corresponded to the formula

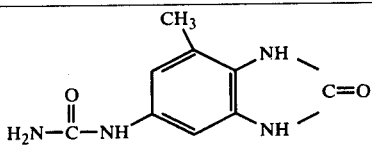

| Analysis: | C | H | N |
|---|---|---|---|
| Found: | 52.1 | 4.81 | 26.9 |
| Calculated: | 52.47 | 4.9 | 27.2 |
| $C_9H_{10}N_4O_2$ molecular weight: 206 | | | |

EXAMPLE 6

131 Parts of finely ground 6-bromo-2,4-dinitro-aniline were hydrogenated together with 30 parts of glacial acetic acid in 600 parts by volume of water and 20 parts of a commercial-type nickel catalyst in a hydrogenation autoclave, while taking care that the temperature did not exceed 90° C.

Evidence for the 6-bromo-1,2,4-triamino-benzene obtained after the usual work-up and reaction with urea resulted in 108 parts of a compound having a melting point above 340° C. and corresponding to the formula

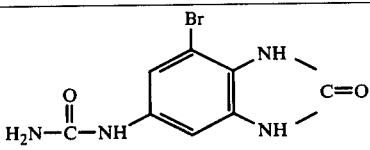

| Analysis: | C | H | N |
|---|---|---|---|
| Found: | 35.81 | 2.62 | 26.0 |
| Calculated: | 35.45 | 2.59 | 25.85 |
| $C_8H_7N_4O_2Br$ molecular weight: 271 | | | |

We claim:

1. A process for preparing a 1,2,4-triamino-benzene which comprises hydrogenating in the presence of a hydrogenation catalyst a 2,4-dinitro-aniline of the formula:

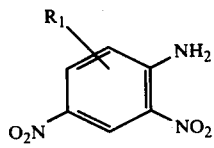

wherein $R_1$, if in the 6-position, is hydrogen, halogen or methyl, and if in the 5-position, is hydrogen or methyl, in water containing a carboxylic acid of the formula

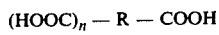

$(HOOC)_n — R — COOH$ wherein n is 0 or 1 and, if n is 0, R is hydrogen, phenyl or alkyl of 1 to 4 carbon atoms, and if n is 1, R is a direct bond, phenylene or alkylene of 1 to 4 carbon atoms.

2. A process according to claim 1 wherein $R_1$ is chlorine in the 6-position.

3. A process according to claim 1 wherein the hydrogenation is carried out at a temperture of from 50° to 130° C.

4. A process according to claim 1 wherein the hydrogenation is carried out at a temperature of from 70° to 100° C.

5. A process according to claim 1 wherein at least one molar equivalent of carboxylic acid is used per mole of dinitro-aniline.

6. A process according to claim 1 wherein said carboxylic acid is adipic acid.

7. A process according to claim 1 wherein said carboxylic acid is acetic acid.

8. A process according to claim 1 wherein said carboxylic acid is terephthalic acid.

9. A process according to claim 1 wherein said carboxylic acid is benzoic acid.

10. A process according to claim 1 wherein about 700 to 800 parts by volume of water are used per mol of dinitro-aniline.

11. A process for preparing a 1,2,4-triaminobenzene which comprises hydrogenating a 2,4-dinitro-aniline of the formula:

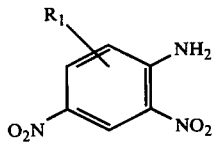

wherein $R_1$, if in the 6-position, is hydrogen, halogen or methyl, and if in the 5-position, is hydrogen or methyl, in the form of an aqueous suspension or dispersion and in the presence of a nickel catalyst and an aqueous carboxylic acid of the formula

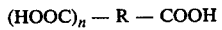

$(HOOC)_n — R — COOH$ wherein n is 0 or 1 and, if n is 0, R is hydrogen, phenyl or alkyl of 1 to 4 carbon atoms, and if n is 1, R is a direct bond, phenylene or alkylene of 1 to 4 carbon atoms.

12. A process for preparing 1,2,4-triamino-benzene which comprises dispersing in water particulate 2,4-dinitro-aniline of the formula:

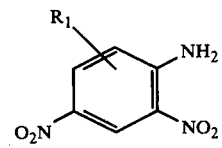

wherein $R_1$, if in the 6-position, is hydrogen, halogen or methyl, and if in the 5-position, is hydrogen or methyl, incorporating in the resulting reaction mixture a nickel hydrogenation catalyst and an aqueous carboxylic acid of the formula:

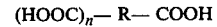

$(HOOC)_n — R — COOH$ wherein n is 0 or 1 and, if n is 0, R is hydrogen, phenyl or alkyl of 1 to 4 carbon atoms, and if n is 1, R is a direct bond, phenylene or alkylene of 1 to 4 carbon atoms, and hydrogenating said reaction mixture at an elevated temperature and pressure to form said triamino-benzene.

* * * * *